(12) United States Patent
Suarez et al.

(10) Patent No.: US 8,460,277 B2
(45) Date of Patent: Jun. 11, 2013

(54) END EFFECTOR WITH RELEASE ACTUATOR

(75) Inventors: Joseph Suarez, Plantation, FL (US); Brian Schmitz, Fort Lauderdale, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 661 days.

(21) Appl. No.: 12/644,990

(22) Filed: Dec. 22, 2009

(65) Prior Publication Data

US 2010/0168723 A1 Jul. 1, 2010

Related U.S. Application Data

(60) Provisional application No. 61/203,475, filed on Dec. 23, 2008.

(51) Int. Cl.
*H01H 3/20* (2006.01)

(52) U.S. Cl.
USPC ............... 606/1; 606/42; 200/43.17; 200/334

(58) Field of Classification Search
None
See application file for complete search history.

(56) References Cited

U.S. PATENT DOCUMENTS

| | | | |
|---|---|---|---|
| 3,353,771 A | 11/1967 | Te Bow | |
| 4,091,880 A * | 5/1978 | Troutner et al. | 173/217 |
| 4,290,574 A | 9/1981 | Archibald | |
| 4,360,974 A | 11/1982 | De Cuissart | |
| 4,541,178 A | 9/1985 | White | |
| 4,610,020 A | 9/1986 | La Fiandra | |
| 4,770,497 A | 9/1988 | Brown | |
| 5,046,375 A | 9/1991 | Salisbury et al. | |
| 5,161,424 A | 11/1992 | Saberton et al. | |
| 5,167,464 A | 12/1992 | Voellmer | |
| 5,207,114 A | 5/1993 | Salisbury et al. | |
| 5,383,875 A * | 1/1995 | Bays et al. | 606/1 |
| 5,513,946 A | 5/1996 | Sawada et al. | |
| 5,778,730 A | 7/1998 | Solomon et al. | |
| 5,794,487 A | 8/1998 | Solomon et al. | |
| 5,816,770 A | 10/1998 | Itagaki | |
| 6,152,941 A | 11/2000 | Himes et al. | |

(Continued)

FOREIGN PATENT DOCUMENTS

| EP | 1 815 949 A1 | 8/2007 |
|---|---|---|
| EP | 1 815 950 A1 | 8/2007 |

(Continued)

OTHER PUBLICATIONS

U.S. Appl. No. 12/654,518, filed Dec. 22, 2009, Bennett et al.

(Continued)

*Primary Examiner* — Henry M Johnson, III
*Assistant Examiner* — Scott T Luan
(74) *Attorney, Agent, or Firm* — Foley & Lardner LLP

(57) ABSTRACT

An end effector is disclosed that includes a tool including a drive configured to be coupled to and drive an engaging member for engaging a workpiece and a release member configured to be displaced to permit decoupling of the engaging member from the drive. The end effector also includes a housing configured to receive at least a portion of the tool and a release actuator disposed at least partially outside of the housing and coupled to the housing to permit movement between a first position and a second position to displace the release member to permit decoupling of the engaging member from the drive.

23 Claims, 11 Drawing Sheets

U.S. PATENT DOCUMENTS

| | | |
|---|---|---|
| 6,236,788 B1 | 5/2001 | Moisel |
| 6,370,974 B1 | 4/2002 | Jourtchenko et al. |
| 6,394,998 B1 | 5/2002 | Wallace et al. |
| 6,668,466 B1 | 12/2003 | Bieg et al. |
| 6,688,189 B2 | 2/2004 | Hashimoto et al. |
| 6,729,589 B2 | 5/2004 | Shelef |
| 6,826,324 B2 | 11/2004 | Steinberg et al. |
| 7,021,167 B2 | 4/2006 | Liesegang |
| 7,316,681 B2 | 1/2008 | Madhani et al. |
| 7,959,162 B2 * | 6/2011 | Smith et al. ............... 279/74 |
| 2002/0035372 A1 | 3/2002 | Zisterer et al. |
| 2003/0075790 A1 | 4/2003 | Steinberg et al. |
| 2003/0104886 A1 | 6/2003 | Gajewski |
| 2003/0152661 A1 | 8/2003 | Yu et al. |
| 2004/0049205 A1 | 3/2004 | Lee et al. |
| 2006/0016061 A1 | 1/2006 | Shelef |
| 2006/0047272 A1 * | 3/2006 | McPherson et al. .............. 606/1 |
| 2007/0089557 A1 | 4/2007 | Solomon et al. |
| 2007/0142969 A1 | 6/2007 | Devengenzo et al. |
| 2007/0299427 A1 | 12/2007 | Yeung et al. |
| 2008/0010706 A1 * | 1/2008 | Moses et al. ............... 901/8 |
| 2008/0021440 A1 | 1/2008 | Solomon |
| 2008/0058861 A1 | 3/2008 | Cooper et al. |
| 2008/0087871 A1 | 4/2008 | Schena |
| 2008/0248907 A1 | 10/2008 | Cottrell |
| 2008/0278105 A1 | 11/2008 | Somes |
| 2008/0287862 A1 | 11/2008 | Weitzner et al. |
| 2010/0166496 A1 | 7/2010 | Bennett et al. |
| 2010/0170361 A1 | 7/2010 | Bennett et al. |
| 2010/0170362 A1 | 7/2010 | Bennett et al. |
| 2011/0174097 A1 | 7/2011 | Bergamasco et al. |

FOREIGN PATENT DOCUMENTS

| | | |
|---|---|---|
| EP | 1 915 966 A1 | 4/2008 |
| WO | WO 2010-074739 | 7/2010 |
| WO | WO 2010-074742 | 7/2010 |
| WO | WO 2010-074744 | 7/2010 |
| WO | WO 2010-075404 | 7/2010 |

OTHER PUBLICATIONS

International Search Report mailed Mar. 22, 2010 in PCT/US2009/069231, 4 pages.
International Search Report mailed May 7, 2010 in PCT/US2009/006655, 4 pages.
International Search Report mailed May 7, 2010 in PCT/US2009/006659, 4 pages.
International Search Report mailed May 7, 2010 in PCT/US2009/006661, 4 pages.
PCT Written Opinion mailed Mar. 22, 2010 in PCT/US2009/069231, 5 pages.
PCT Written Opinion mailed May 7, 2010 in PCT/US2009/006655, 6 pages.
PCT Written Opinion mailed May 7, 2010 in PCT/US2009/006659, 6 pages.
PCT Written Opinion mailed May 7, 2010 in PCT/US2009/006661, 6 pages.

* cited by examiner

END EFFECTOR WITH RELEASE ACTUATOR

CROSS-REFERENCE TO RELATED PATENT APPLICATIONS

This application claims priority to U.S. Provisional Patent Application Ser. No. 61/203,475, filed on Dec. 23, 2008, which is hereby incorporated by reference in its entirety.

BACKGROUND

1. Field of Invention

The present disclosure relates generally to tools or end effectors. More specifically, the present disclosure relates to a mechanism that allows for the selective release of an engaging member, such as a tool bit, from a drive of the tool or end effector.

2. Description of Related Art

Tools or, more specifically, end effectors can be motorized devices that are equipped with a tool bit suitable for accommodating the intended use of the end effector. For example, an end effector may include a tool bit such as a burr, a drill bit, and/or a saw blade. Such an end effector may be used in a variety of applications, including as a surgical tool for performing certain surgical procedures. When used in a surgical setting, the end effector may be used in minimally invasive procedures to selectively remove small sections of hard or soft tissue or to separate sections of tissue.

The end effector includes a motor that is coupled to and configured to drive the tool bit. The coupling between the motor and the tool bit is often removable so that the tool bit can be replaced when worn or when another tool bit may be more suitable for the task. To facilitate the removable coupling, a release mechanism, such as a chuck or collet, may be provided to releasably secure the tool bit relative to the motor. Such release mechanisms may require a separate tool (e.g., wrench, chuck key, etc.) in order to release or tighten the mechanism about the tool bit, may require some sort of disassembly of the end effector in order to reach the release mechanism, and/or may be configured to be released and tightened by hand. In the case of release mechanisms configured to be actuated by hand, the release mechanism can be relatively small and difficult to grasp by a user, particularly in a surgical setting where a surgeon may be wearing gloves covered in bodily fluids from the surgical procedure.

SUMMARY

An embodiment of the invention relates to an end effector including a tool including a drive configured to be coupled to and drive an engaging member for engaging a workpiece and a release member configured to be displaced to permit decoupling of the engaging member from the drive. The end effector also includes a housing configured to receive at least a portion of the tool and a release actuator disposed at least partially outside of the housing and coupled to the housing to permit movement between a first position and a second position to displace the release member to permit decoupling of the engaging member from the drive.

Another embodiment of the invention relates to a tool including a housing configured to at least partially receive a drive having a release member configured to be displaced to permit decoupling of an engaging member from the drive. The tool also includes a first lever disposed at least partially outside of the housing and coupled to the housing about a first pivot shaft defining a first axis of rotation to permit movement between a first position and a second position to activate the drive. The tool further includes a second lever disposed at least partially outside of the housing and coupled to the housing about a second pivot shaft defining a second axis of rotation to permit movement between a third position and a fourth position to displace the release member to permit decoupling of the engaging member from the drive. The second axis of rotation is substantially parallel to the first axis of rotation.

Another embodiment of the invention relates to a surgical tool including a housing, a drive configured to be coupled to and drive an engaging member for engaging a workpiece, a release member configured to be displaced to permit decoupling of the engaging member from the drive and a release actuator disposed at least partially outside of the housing and coupled to the housing to permit movement between a first position and a second position to displace the release member to permit decoupling of the engaging member from the drive.

BRIEF DESCRIPTION OF THE DRAWINGS

The accompanying drawings, which are incorporated and constitute a part of this specification, illustrate embodiments of the invention and together with the description serve to explain aspects of the invention.

DETAILED DESCRIPTION

Figure 1:
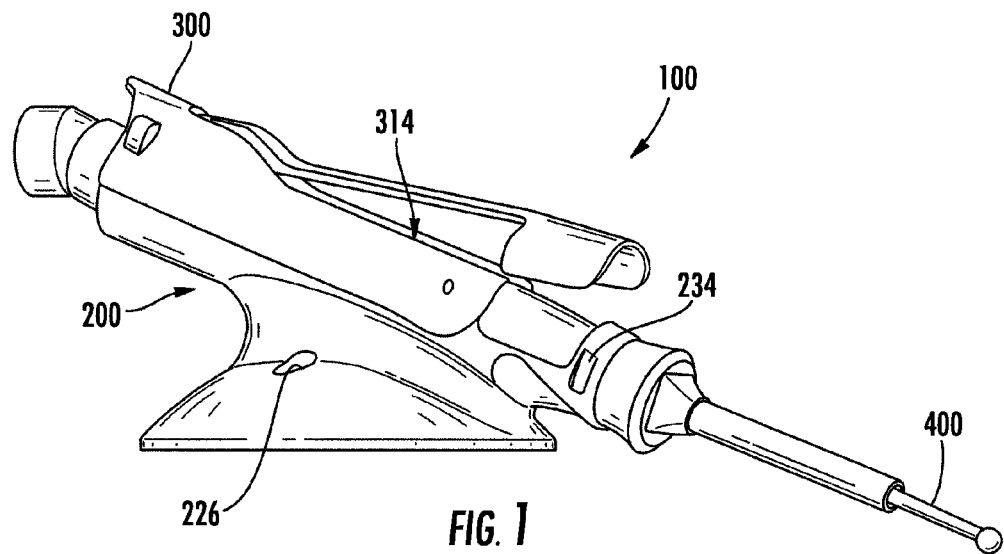
FIG. 1 is a perspective view of a tool shown according to an exemplary embodiment as an end effector assembly.

Presently preferred embodiments of the invention are illustrated in the drawings. An effort has been made to use the same or like reference numbers throughout the drawings to refer to the same or like parts.

The present invention relates to a tool or end effector, hereinafter referred to merely as an end effector for simplicity of explanation. The end effector can be particularly advantageous in a robotic surgical system. Although this specification describes the end effector in the environment of a robotic surgical system, it should be understood that the end effector is applicable to other types of robotic systems, including those used for surgical and non-surgical applications, as well as to non-robotic systems or applications. The present invention is not limited to the details or methodology set forth in the description or illustrated in the figures.

Overview of a Robotic Surgical System

Figure 2:
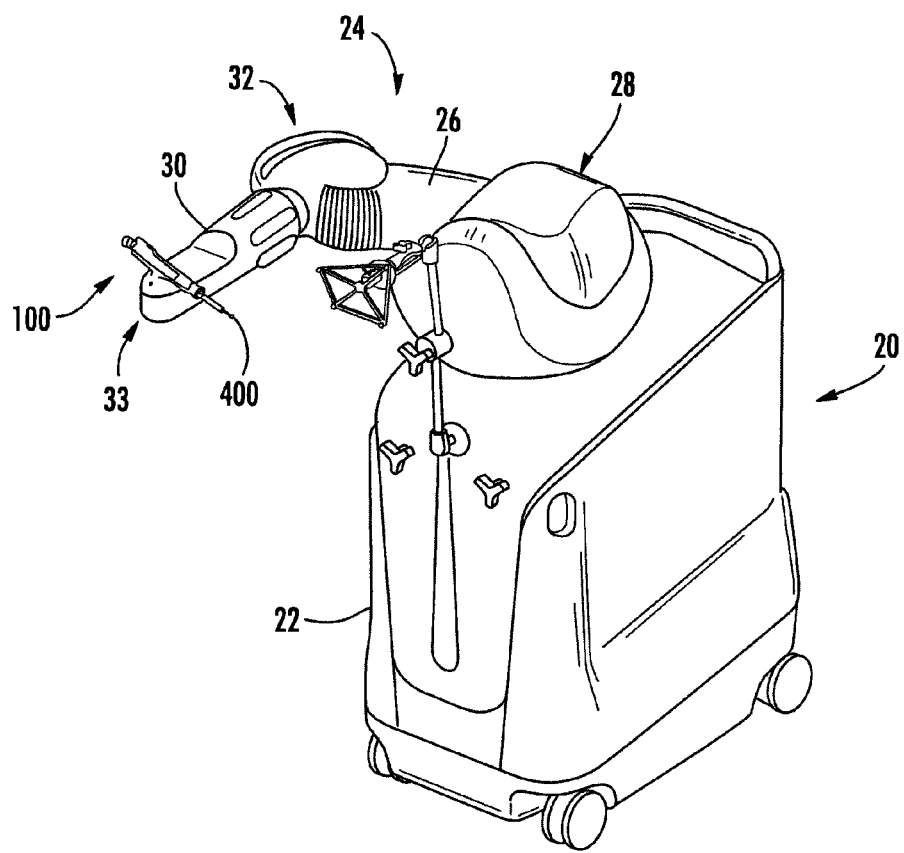
FIG. 2 is a perspective view of the end effector of FIG. 1 coupled to an articulated arm of a surgical robot.

FIG. 2 illustrates an example of a robotic surgical system 20 in which an end effector 100 according to the present invention can be used. The robotic surgical system 20 preferably includes a main body 22 upon which is mounted an articulated robotic arm 24 that can be used in an interactive manner by a surgeon to perform a surgical procedure on a patient. In a preferred embodiment, the robotic surgical system 20 is the RIO® Robotic Arm Interactive Orthopedic System manufactured by MAKO Surgical Corp. of Fort Lauderdale, Fla. The robotic arm 24 is preferably a haptic device that works in combination with a computer aided navigation system (not shown) and a tracking device (not shown). For example, as described in U.S. patent application Ser. No. 11/357,197 (Pub. No. US 2006/0142657), filed Feb. 21, 2006, and hereby incorporated by reference herein in its entirety, tool bit 400 (such as a cutting burr, a drill, a clamp, scalpel, laser, or other tool bit) is coupled to the robotic arm 24. The surgeon manually moves the robotic arm 24 to manipulate the tool bit 400 to perform a surgical task on the patient, such as bone cutting for a joint replacement operation. As the surgeon manipulates the tool bit 400, the robotic arm can provide haptic (or force) feedback to limit the surgeon's ability to move the tool bit 400 beyond a predefined virtual cutting boundary, which results in highly accurate and repeatable bone cuts. The robotic arm 24 can work in a passive manner and provide haptic feedback only when the surgeon attempts to cut bone that lies outside the virtual cutting boundary. The haptic feedback can be generated by one or more actuators (e.g., motors; not shown) in the robotic arm and transmitted to the surgeon via a flexible transmission (not shown), such as a tension element transmission. When the robotic arm 24 is not providing haptic feedback, the robotic arm 24 can be freely moveable by the surgeon.

The robotic arm 24 preferably includes a first segment 26 coupled to the main body 22 and maneuverable relative to the main body 22 about a first joint assembly 28. The robotic arm 24 can further include a second segment 30 coupled to the first segment 26 and maneuverable relative to the first segment 26 about a second joint assembly 32. End effector 100 can be mounted to second segment 30 about a third joint assembly 33. Some or all of the joint assemblies 28, 32, 33 preferably include multiple joints that combine to provide six degrees of freedom of movement, which may enable surgical access to difficult to reach bone structures through minimally invasive incisions (e.g., less than appropriately four to six inches in length).

The Tool or End Effector

Referring to FIG. 1, in the embodiment illustrated, the end effector 100 is a surgical tool intended to be used in performing surgical procedures. It should be understood that, although the present invention will be described in detail herein with reference to an end effector, and particularly to an end effector used as a surgical device, the present invention may be applied to, and find utility in, other types of tools including, but not limited to hand-held surgical devices, hand-power tools (e.g., drills, saws, routers, etc.), standalone power tools, etc. Therefore, the scope of the invention is not limited to an end effector for surgical procedures.

The end effector 100 preferably includes a casing or housing 200 to which a release actuator 300 (e.g., lever, etc.) is coupled. The release actuator 300 is disposed at least partially outside of the housing 200 and is configured to be selectively moved relative to the housing 200 between a first position (shown in FIG. 1) and a second position (shown in FIG. 12). A drive, such as a motor 500 (shown, e.g., in FIGS. 7-9), is at least partially enclosed or encased within housing 200. The motor 500 drives an engaging member (e.g., implement, attachment, instrument, etc.), shown as a tool bit 400, used for engaging a workpiece. The end effector 100 includes a first attachment mechanism located within the housing 200 for removably attaching tool bit 400 to the motor 500. The first attachment mechanism includes a release member that is configured to be selectively moved in an axial direction relative to the motor 500 and/or the housing 200. To release or otherwise decouple the tool bit 400 from the motor 500, an operator selectively moves the release actuator 300 to the second position thereby axially displacing the release member of the first attachment mechanism to permit decoupling of the tool bit 400. Once decoupled, the tool bit 400 can be removed from the end effector 100. The size, positioning, shape and/or movement of the release actuator 300 may provide an operator of the end effector 100 with an efficient and easy to use means for decoupling the tool bit 400 from the motor 500 during a surgical procedure.

Figure 3:
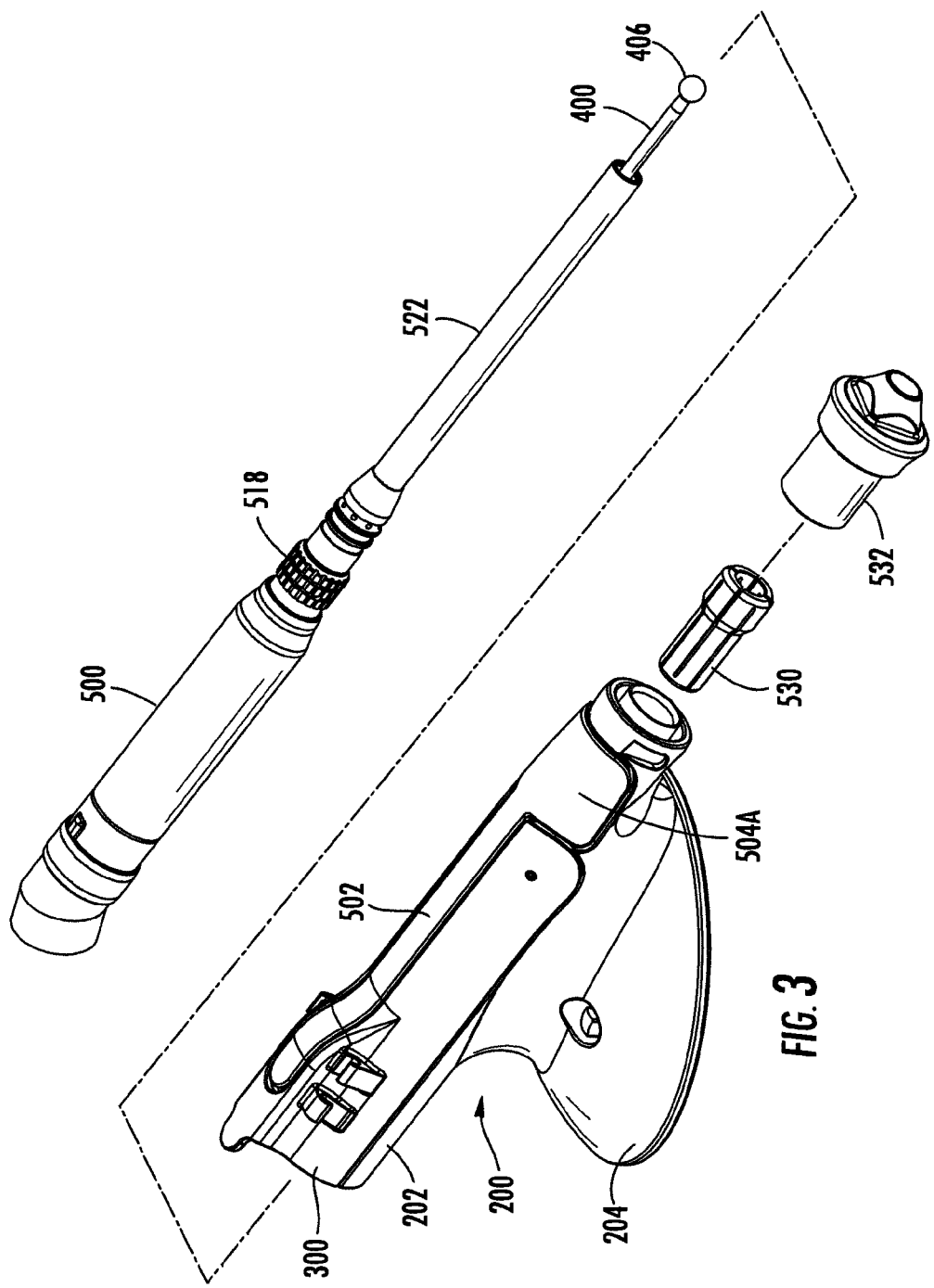
FIG. 3 is an exploded perspective view of the end effector assembly of FIG. 1.
Figure 4:
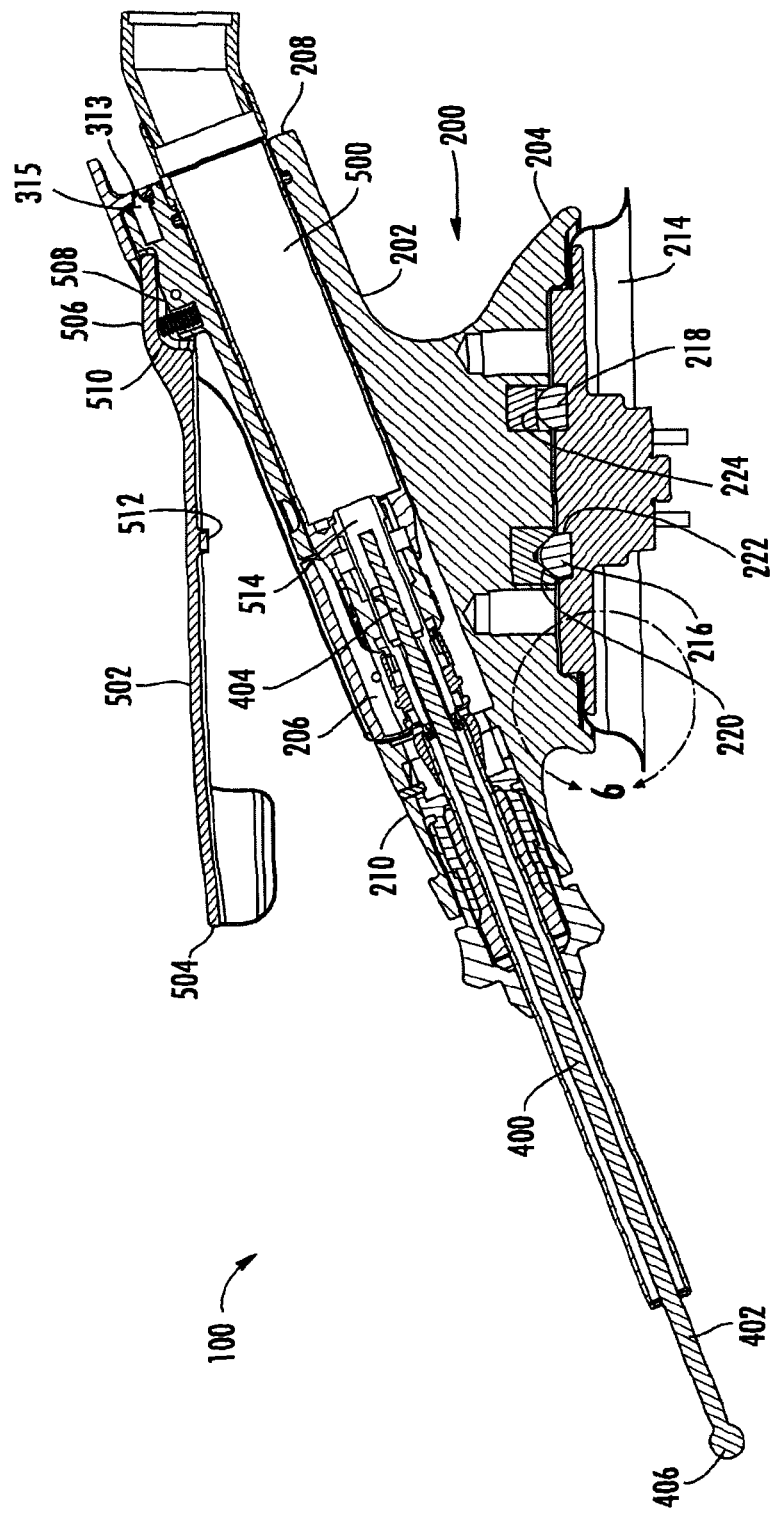
FIG. 4 is a cross sectional view of the end effector assembly shown in FIG. 1 with the end effector assembly in an off position.
Figure 5:
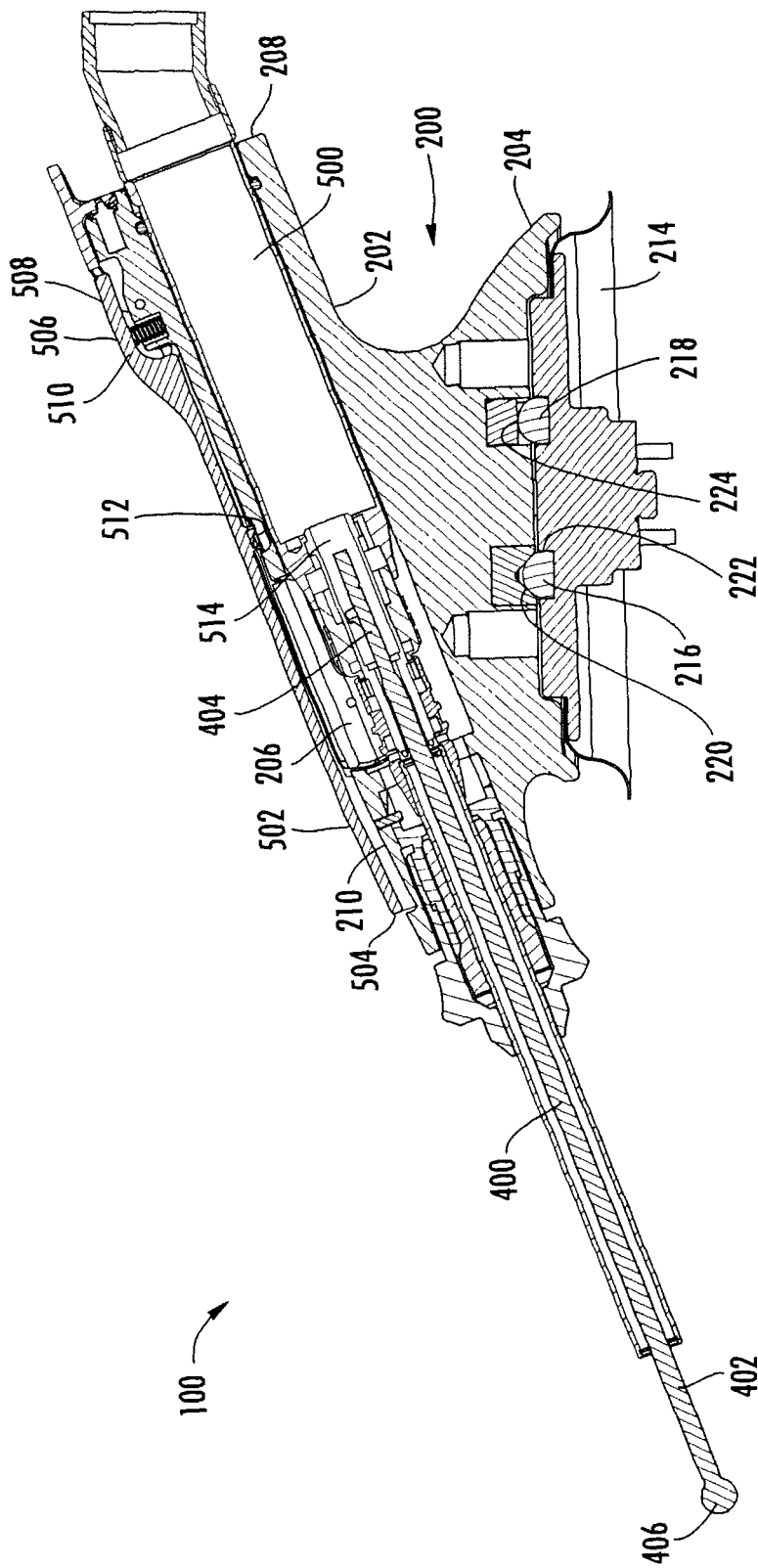
FIG. 5 is a cross sectional view of the end effector assembly shown in FIG. 1 with the end effector assembly in an on position.

FIGS. 3 through 16 illustrate in greater detail the features of the end effector 100. Referring to FIGS. 3 through 5, the housing 200 is shown according to an exemplary embodiment. The housing 200 includes a first portion, shown as a main body 202, and a second portion (e.g., mounting portion, etc.), shown as a support base 204. According to an exemplary embodiment, the main body 202 is generally cylindrical in shape and defines a chamber or cavity 206 that is configured to receive a drive, such as an electrically driven motor 500. To accommodate the motor 500, the main body 202 includes an opening at a rear end 208 through which the motor 500 can be inserted into the housing. The main body 202 is further shown as having a neck 210 at a front end of the housing that has a reduced diameter relative to the rear end 208. According to the embodiment illustrated, an outer periphery or contour of the main body 202 is ergonomically shaped to fit in a palm of a typical operator (e.g., surgeon, etc.) so that the operator can effectively grasp the end effector 100 to guide the robotic arm 24 during a surgical procedure while the end effector 100 remains mounted to the robotic arm 24.

The support base 204 is rigidly coupled to and provided at a lower portion of the main body 202. According to an exemplary embodiment, the support base 204 is integrally formed with the main body 202 to provide a one-piece unitary housing. According to the various alternative embodiments, the support base 204 may be a separate component that is coupled to or otherwise supports the main body 202. The support base 204 is fastened to a mount 214 provided at an end of the second segment 30 of the robotic arm 24. The support base 204 is fastened to the mount 214 via any suitable coupling mechanism. According to the embodiment illustrated, the coupling mechanism is a semi-kinematic coupling including a first semi-cylindrical projection 216 and a second semi-cylindrical projection 218 extending from the mount 214. The first and second surfaces 220, 222 form a V-shaped receiving area the first semi-cylindrical projection 216. A third surface 224 forms a flat receiving area for second semi-cylindrical projection 218. The mount 214 and the support base 204 are clamped together using one or more fasteners (e.g., bolts, etc.) extending into the receiving ports 226 (shown in FIG. 1) in the support base 204.

According to an exemplary embodiment, the main body 202 is supported at an angle relative to the support base 204. For example, according to the embodiment illustrated, the main body 202 is angled downward relative to the support base 204 between the rear end 208 and the neck 210 at an angle of approximately 30 degrees. Such a configuration may help align the tool bit 400 with the workpiece after the end effector 100 is mounted to the robotic arm 24. According to the various alternative embodiments, the main body 202 may be supported at any angle relative to the support base 204. According to further alternative embodiments, the support base 204 may be eliminated and the housing 200 may only include the main body 202.

Figure 6:
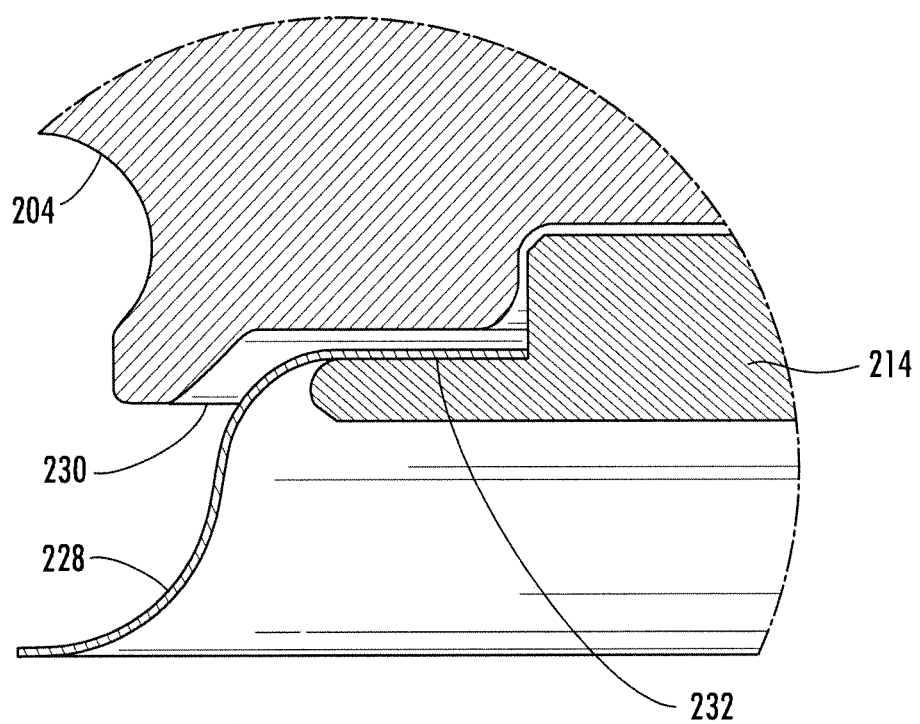
FIG. 6 is a partial detailed view of a mounting arrangement of the end effector assembly of FIG. 1.

Referring to FIG. 6, a covering or shielding element 228 can be disposed between a first clamping surface 230 on the support base 204 and a second clamping surface 232 on the mount 214. According to an exemplary embodiment, the shielding element 228 is relatively elastic (e.g., plastic, etc.) and does not substantially affect the accuracy of the semi-kinematic coupling. The shielding element 228 may serve as a sterile drape configured to protect surfaces of end effector 100 or the robotic arm from dust, dirt or other contaminants. The shielding element 228 may fully surround the support base 204, or alternatively, may only partially surround the support base 204.

Referring back to FIGS. 4 and 5, the motor 500 is at least partially received within the cavity 206 of the main body 202. According to the embodiment illustrated, the motor 500 is entirely enclosed by the main body 202. The motor 500 may be configured to operate, for example, at a single speed or a number of different speeds. The power for energizing the motor 500 within the end effector 100 may come from the robotic surgical system 20 or any other suitable power source. For example, the robotic surgical system 20 may be used to selectively energize the end effector 100 in response to an operator-initiated command and may further monitor the operation of the end effector 100.

The on/off operation and/or speed of the motor 500 preferably is controlled by a drive actuator or user interface (e.g., trigger, lever, push button, toggle switch, etc.), shown as a hand switch 502, that is coupled to the main body 202 of the housing 200. According to an exemplary embodiment, a cable (not shown) is connected between the motor 500 and the robotic surgical system 20 to provide the conductive paths for the signals exchanged between the end effector 100 and the robotic surgical system 20. These signals may include signals generated by the end effector 100 in response to the state of the hand switch 502 and/or signals sent for activating the motor 500. According to the various alternative embodiments, the end effector 100 may be configured so that no signals are exchanged between the end effector 100 and the robotic surgical system 20. According to further alternative embodiments, the end effector 100 may not be fitted with a user interface for actuating the motor 500. Instead, the on/off state and/or motor speed of the motor 500 may be controlled by the actuation of an interface that is remote from the end effector 100 (e.g., the interface may be one or more pedals of a foot switch assembly).

According to an exemplary embodiment, the hand switch 502 is in the form of a lever arm that extends forward along the length of the main body 202. The hand switch 502 has a first end 504 that is configured to be engaged by an operator and a second end 506 that is coupled to an upper surface of the main body 202 at the rear end 208. The second end 506 is coupled to the main body 202 about a pivot shaft 508 defining an axis of rotation that is substantially perpendicular to a longitudinal or central axis of the main body 202. The hand switch 502 is configured to rotate about the pivot shaft 508 between a first position (e.g., an off position, etc.), shown in FIG. 4, and a second position (e.g., an on position, etc.), shown in FIG. 5. A biasing element (e.g., spring, etc.), shown as a compression spring 510, is located between the main body 202 and the second end 506 and is configured to bias the hand switch 502 so that the first end 504 is normally pivoted away from the main body 202. A first sensor element, shown as a magnet 512, is coupled to an underside of the hand switch 502. The position of the magnet 512, and thus the position of the hand switch 502, is monitored by a second sensor element (e.g., a Hall effect sensor, etc.) that is provided on the main body 202. According to an exemplary embodiment, the second sensor is incorporated into the motor 500.

To activate the motor 500, an operator presses down on the first end 504 of the hand switch 502 with a force sufficient to overcome the biasing force of the compression spring 510. The hand switch 502 is rotated downward about the pivot shaft 508 until the magnet 512 is close enough to the second sensor element so that the second sensor element will detect the proximity of the magnet 512. When the second sensor element detects the magnet 512, a control circuit is activated for turning on the motor 500. According to an exemplary embodiment, in a case where the motor 500 is capable of operating at multiple speeds, the selective positioning of the hand switch 502 relative to the main body 202 may dictate the desired motor speed (e.g., the more the hand switch 502 is depressed (i.e., the closer the hand switch 502 is to the main body 202), the greater the motor speed, etc.). In such configurations, the proximity of the magnet 512 relative to the second sensor element can then be used to provide an indication of the desired operating speed of the motor 500. According to the embodiment illustrated, the total angular displacement of the hand switch 502 between the first position (shown in FIG. 4) and the second position (shown in FIG. 5) is relatively small (e.g., approximately 20 degrees, etc.) so that an operator can control its positioning with one hand. Additionally, the first end 504 of the hand switch 502 may include lateral projections 504A (see FIG. 10). The projections 504A facilitate the operator's ability to actuate the hand switch 502 by providing increased surface area for the operator to press on (e.g., with a thumb or one or more fingers) to actuate the hand switch 502.

According to an exemplary embodiment, the motor 500 includes a drive spindle or shaft 514 configured to rotate upon activation of the motor 500. The tool bit 400 is configured to be coupled to the drive shaft 514 so as to rotate with the drive shaft 514. The tool bit 400 is configured to be interchangeable, and as such, a releasable coupling is provided between the tool bit 400 and the drive shaft 514. According to the embodiment illustrated, the tool bit 400 is in the form of a cutting burr having a first end 402 that is configured to engage a workpiece (e.g., bone, etc.) and a second end 404 that is configured to be secured to the drive shaft 514. The first end 402 includes an operating tip or head 406 for shaping the workpiece during a surgical procedure. While the operating head 406 is shown as being substantially spherical in shape, the tool bit 400 may have any of a variety of shapes (e.g., cylindrical, trapezoidal, etc.). Further, according to the various alternative embodiments, the tool bit 400 may be any of a variety of instruments including, but not limited to, a drill bit, saw blade, scalpel, clamp, etc. The second end 404 of the tool bit 400 includes a base or shank that is configured to be received within the drive shaft 514.

Figure 7:
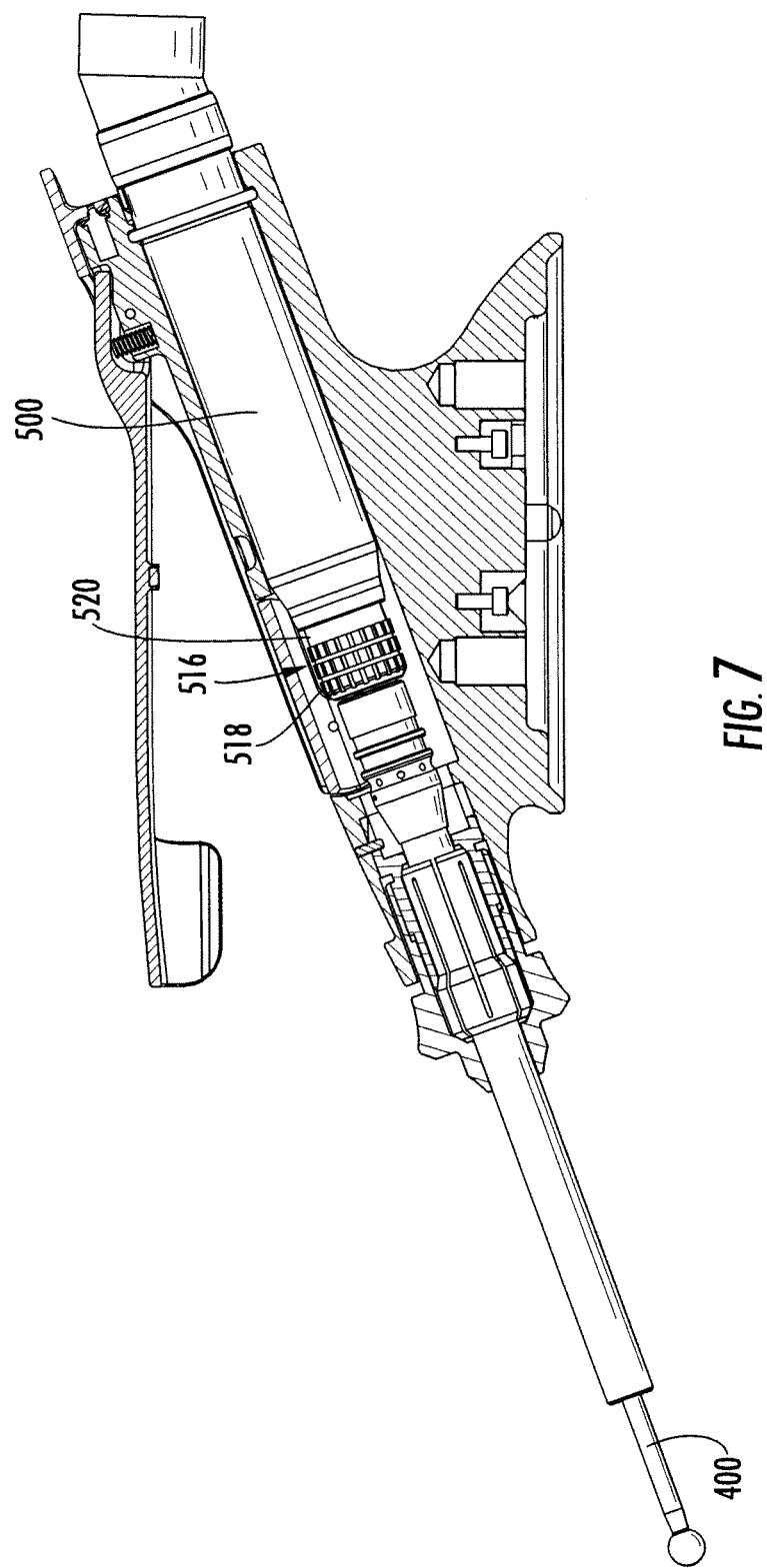
FIG. 7 is a cross sectional view of the end effector assembly of FIG. 1 showing the internal components.
Figure 8:
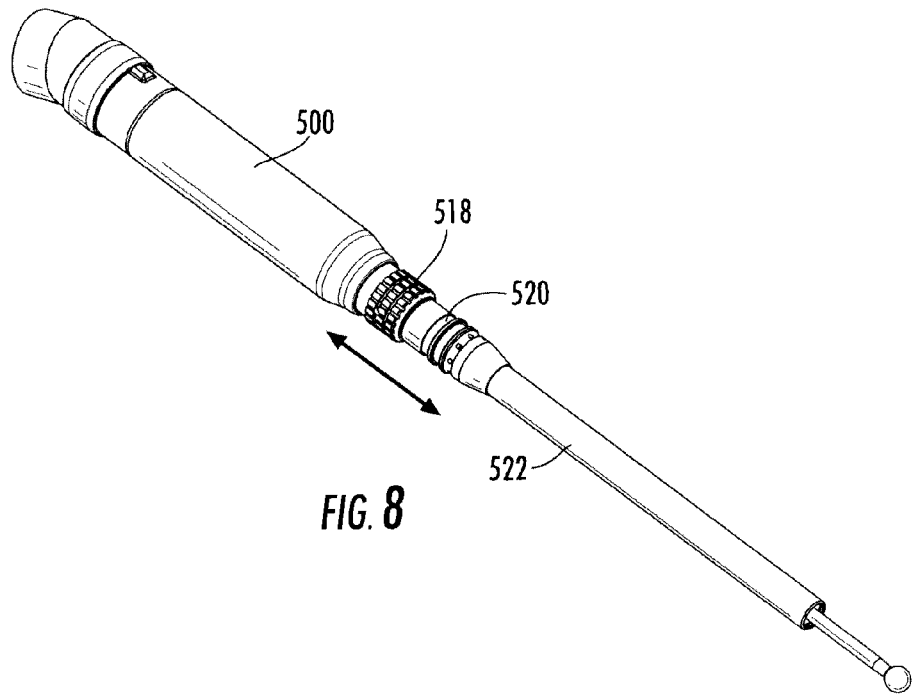
FIG. 8 is a perspective view of a first attachment mechanism that removably couples a tool bit to a drive according to an exemplary embodiment.
Figure 9:
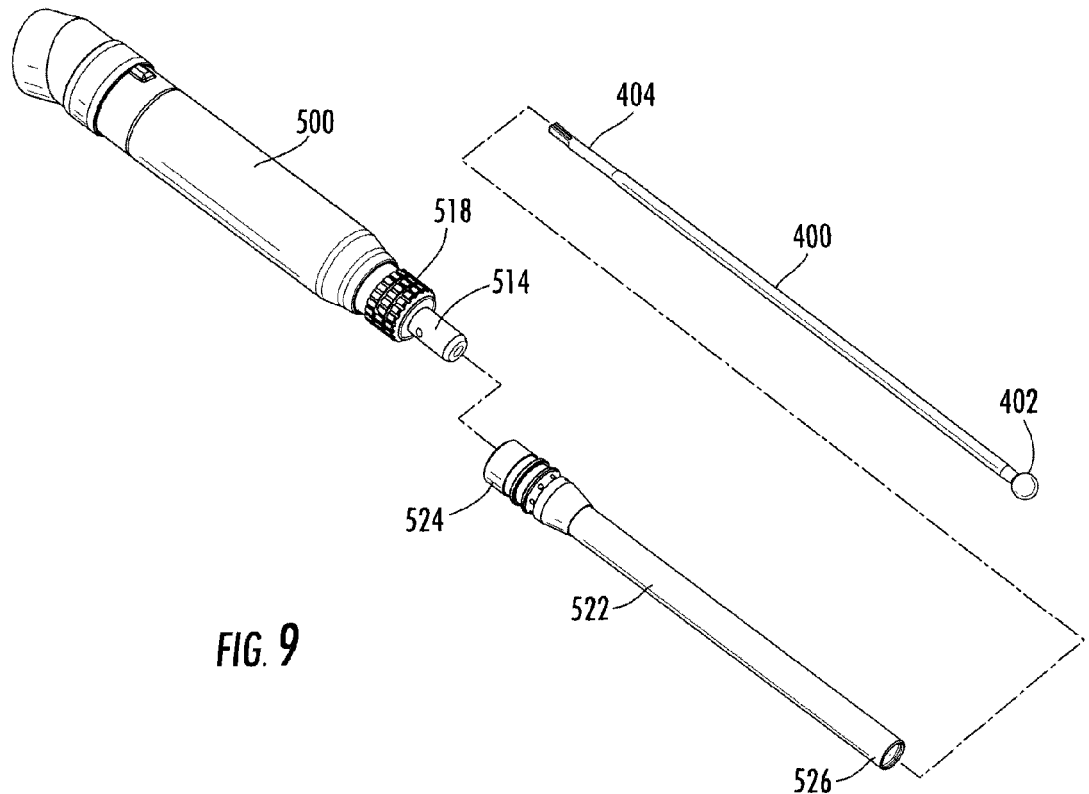
FIG. 9 is an exploded perspective view of the tool bit removed from the drive.

For certain applications it may be desirable to remove and/or replace the tool bit 400 if the operating head 406 becomes dull or otherwise worn. It may also be desirable to interchange the tool bit 400 with a tool bit of a different size and/or configuration. To facilitate the removable coupling of the tool bit 400 to the motor 500, a first attachment mechanism 516 (e.g., coupler) is provided. Referring to FIGS. 7 through 9, the first attachment mechanism 516 is provided at a front or operating end of the motor 500 and includes a release member (e.g., release nut, burr release nut, sleeve, etc.), shown as a collar 518. The collar 518 is disposed around a front housing 520 of the motor 500 and is selectively moveable in an axial direction relative to the front housing 520 between a first or locking position (e.g., a forward most position) and a second or release position (e.g., a rearward most position). The collar 518 is shown as being a tubular member having a substantially circular cross section. A biasing element (e.g., a coil spring, etc.) is disposed between the collar 518 and the front housing 520 to bias the collar 518 forward towards the locking position. In the locking position, the shank at the second end 404 of the tool bit 400 is locked to the motor 500 and cannot fall out. To release and/or reattach the tool bit 400 to the motor 500, the collar 518 is slid back axially along the front housing 520 against the biasing force of the biasing element. Examples of a suitable motor and first attachment mechanism are the motor and attachment mechanism of the eMax Plus electric drive system manufactured by The Anspach Effort®, Inc. of Palm Beach Gardens, Fla.

Figure 10:
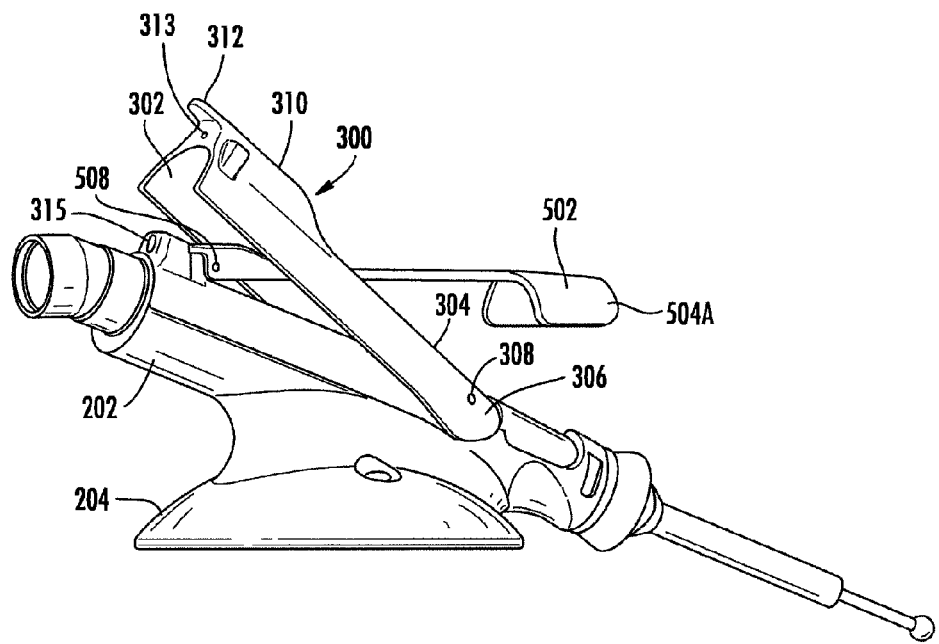
FIG. 10 is a rear perspective view of the end effector assembly of FIG. 1 showing a release actuator according to an exemplary embodiment in an actuated position.
Figure 11:
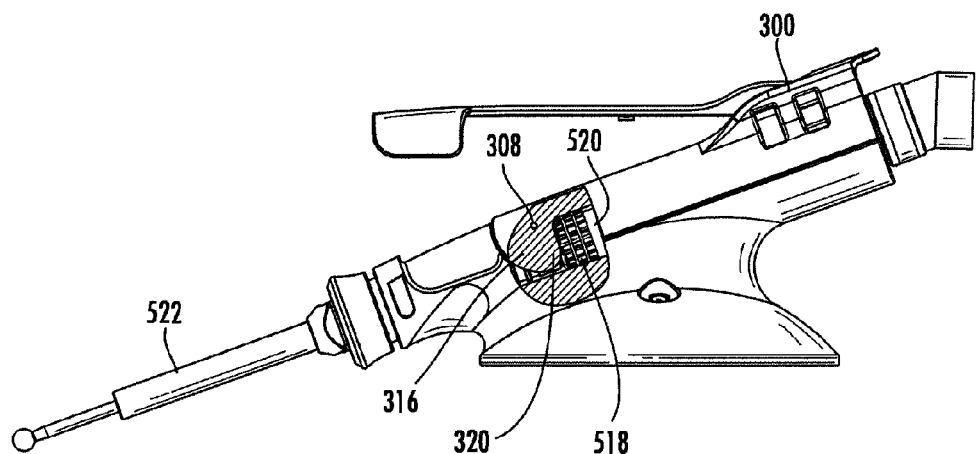
FIG. 11 is a side view of the end effector assembly of FIG. 1 having a cutaway portion to show the positioning of the release actuator when in a locking position.
Figure 12:
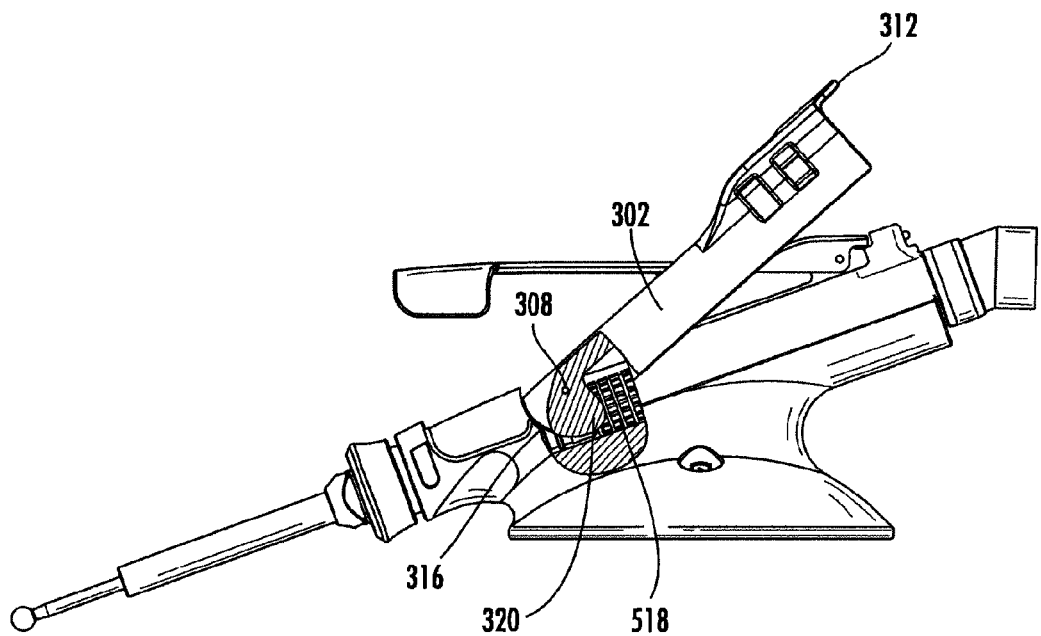
FIG. 12 is a side view of the end effector assembly of FIG. 1 having a cutaway portion to show the positioning of the release actuator when in the actuated position.

To facilitate the movement of the collar 518 between the locking position and the release position by an operator, thereby allowing the operator to change the tool bit 400, the release actuator 300 is provided. Referring to FIGS. 10 through 12, the release actuator 300 is shown according to an exemplary embodiment. The release actuator 300 is disposed at least partially outside of the housing 200 and is configured to be selectively moved relative to the housing 200 between the first position (shown in FIG. 11) and the second position (shown in FIG. 12). When the release actuator 300 is in the first position, the collar 518 is in the locking position and the tool bit 400 is coupled to the motor 500. When the release actuator 300 is in the second position, the collar 518 is in the release position and the tool bit 400 is decoupled from the motor 500.

According to an exemplary embodiment, the release actuator 300 is in the form of a lever that is pivotally coupled to the main body 202 and configured to be rotated by an operator between the first position and the second position. The release actuator 300 is shown as being a substantially symmetrical member including a first portion (e.g., lever, leg, etc.), shown as a first arm 302, provided on a first lateral side of the main body 202 and a second portion (e.g., lever, leg, etc.), shown as a second arm 304, provided on an opposite second lateral side of the main body 202. The first arm 302 and the second arm 304 extend along the length of the main body 202 and define an outer surface of the housing 200 when the release actuator 300 is in the first position. The first arm 302 and the second arm 304 include a contour that substantially corresponds to the outer surface of the main body 202. According to the embodiment illustrated, the first arm 302 and the second arm 304 have curved inner surfaces that substantially match the circular cross section of the main body 202.

The first arm 302 and the second arm 304 each have a first or front end 306 that is coupled to the main body 202 about a pivot shaft 308 defining an axis of rotation that is substantially perpendicular to a longitudinal or central axis of the main body 202 and substantially parallel to the rotational axis of the hand switch 502. The first arm 302 and the second arm 304 are configured to rotate about the pivot shaft 308 as the release actuator 300 rotates between the first position and the second position. The pivot shaft 308 is spaced apart from the pivot shaft 508 so that the release actuator 300 and the hand switch 502 rotate in opposite directions relative to the main body 202. For example, the pivot shaft 308 is located closer to the neck 210 of the main body 202, while the pivot shaft 508 is located closer to the rear end 208.

The first arm 302 and the second arm 304 are coupled to each other at a rear end of the release actuator 300 by a cross support portion 310 that extends laterally between the first arm 302 and the second arm 304. The first arm 302 and the second arm 304 may also be coupled to each other at a front end of the release actuator 300 by another cross support portion (not shown) that extends laterally between the first arm 302 and the second arm 304. The cross support portion 310 includes a hole 313 that receives a plunger 315 projecting outward from the rear of the main body 202 to hold the release actuator 300 in the first position (see FIG. 4). The plunger 315 is biased (e.g., by a spring, etc.) to project outward. The cross support portion 310 further includes a projection, shown as a tab 312, extending outward in a rearward direction from the release actuator 300. The tab 312 is the portion of the release actuator 300 that is configured to be grasped or otherwise engaged by an operator when moving the release actuator 300 from the first position to the second position. With the release actuator 300 in the first position, an operator pulls or pushes the tab 312 upward in an effort to rotate the release actuator 300 about the pivot shaft 308. As the release actuator 300 begins to rotate, the plunger 315 is depressed by an interior portion of the release actuator 300 so that the plunger 315 partially retracts into the main body 202 and thus disengages the hole 313 to allow the release actuator 300 to rotate into the second position (see FIG. 10). Once the cross support portion 310 clears the rear of the main body 202, the plunger 315 returns to its outwardly biased position. Conversely, when the release actuator 300 is rotated from the second position back to the first position, as the interior portion of the release actuator 300 contacts the plunger 315, it depresses the plunger 315 slightly. As the release actuator 300 continues to move toward the first position and the plunger 315 encounters the hole 313, the plunger 315 engages the hole 313 due to its outward bias.

According to an exemplary embodiment, the release actuator 300 overlaps the hand switch 502 such that the release actuator 300 is rotated down on top of the hand switch 502. Such a configuration may allow the release actuator 300 and the hand switch 502 to occupy substantially the same footprint on the main body 202. To accommodate the hand switch 502, the first arm 302 and the second arm 304 are spaced apart from each other in a lateral direction to define an elongated gap or slot 314 (shown in FIG. 1) for receiving the hand switch 502. The slot 314 is sized to provide sufficient clearance so that the hand switch 502 can be actuated between its first and second positions when the release actuator 300 is in the first position.

The release actuator 300 also includes one or more members that are configured to engage the collar 518 for displacing the collar 518 when the release actuator 300 is moved from the first portion to the second position. Such members may be configured to engage the collar 518 directly or indirectly. According to an exemplary embodiment, the members are in the form of a pair of cams 316 comprising a first cam 316 and a second cam 316 that are disposed on opposite sides of the main body 202. The first cam 316 is coupled to the front end 306 of the first arm 302, while the second cam 316 is coupled to the front end of the second arm 304. The first cam 316 and the second cam 316 extend downward from the first arm 302 and the second arm 304 respectively and are located within the main body 202. The front and bottom edges of the first cam 316 and the second cam 316 are curved to provide clearance and allow for the rotation movement of the cams within the main body 202. According to the embodiment illustrated, the first cam 316 and the second cam 316 are integrally formed with the first arm 302 and the second arm 304 respectively, but alternatively may be provided as separate components that are subsequently attached to the first arm 302 and the second arm 304.

According to an exemplary embodiment, the first cam 316 and the second cam 316 are positioned in front of the collar 518 within the main body 202 and include a camming surface 320 that is configured to be positioned adjacent to the collar 518 when the release actuator 300 is in the first position. An example of such positioning is shown in FIG. 11. When the release actuator 300 is rotated about the pivot shaft 308 from the first position to the second position, the first cam 316 and the second cam 316 move in a rearward direction thereby causing the camming surfaces 320 to engage the collar 518. Referring to FIG. 12, as the release actuator 300 continues to be rotated upwards, the camming surfaces 320 push the collar 518 backwards relative to the front housing 520 in an axial direction until the tool bit 400 is decoupled from the motor 500.

Figure 13:
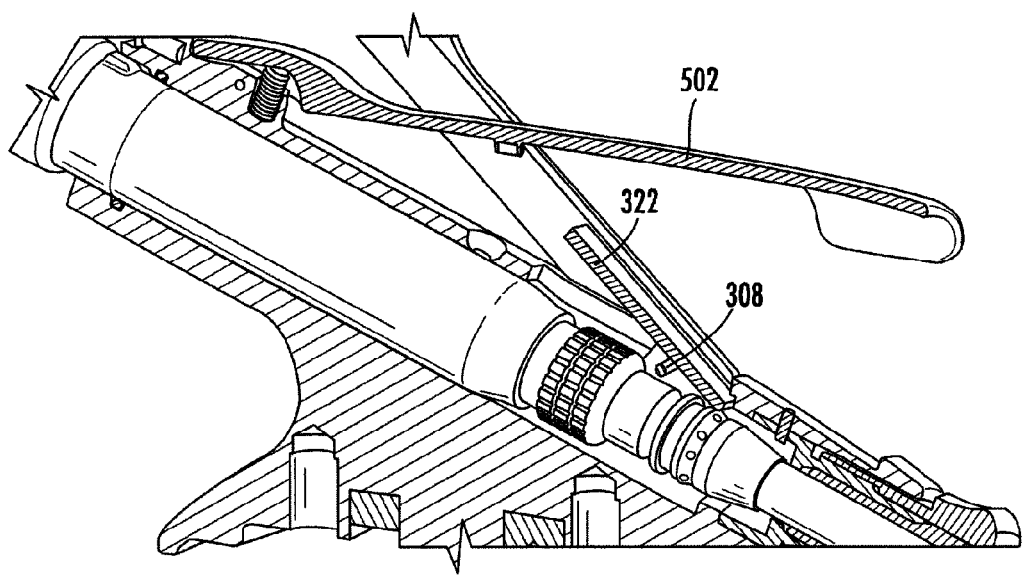
FIG. 13 is a detailed perspective view of the end effector assembly of FIG. 1 showing a blocking feature provided on the release actuator.

To reduce the likelihood that the motor 500 will be inadvertently turned on while the release actuator 300 is in the second position, and the tool bit 400 is being decoupled from the motor 500, the release actuator 300 includes a stop mechanism that is intended to restrict the movement of the hand switch 502 in a direction towards the second position of the hand switch 502 (i.e., the on position). Referring to FIG. 13, the first arm 302 of the release actuator 300 includes an end wall or projection 322 that extends inwardly into the slot 314. The projection 322 is shown as being a substantially rectangular member, but alternatively may be provided as any of a variety of shapes (e.g., cylindrical, trapezoidal, triangular, etc.). According to an exemplary embodiment, the projection 322 is provided on both the first arm 302 and the second arm 304, but alternatively may be provided at only one of the arms 302, 304.

Figure 14:
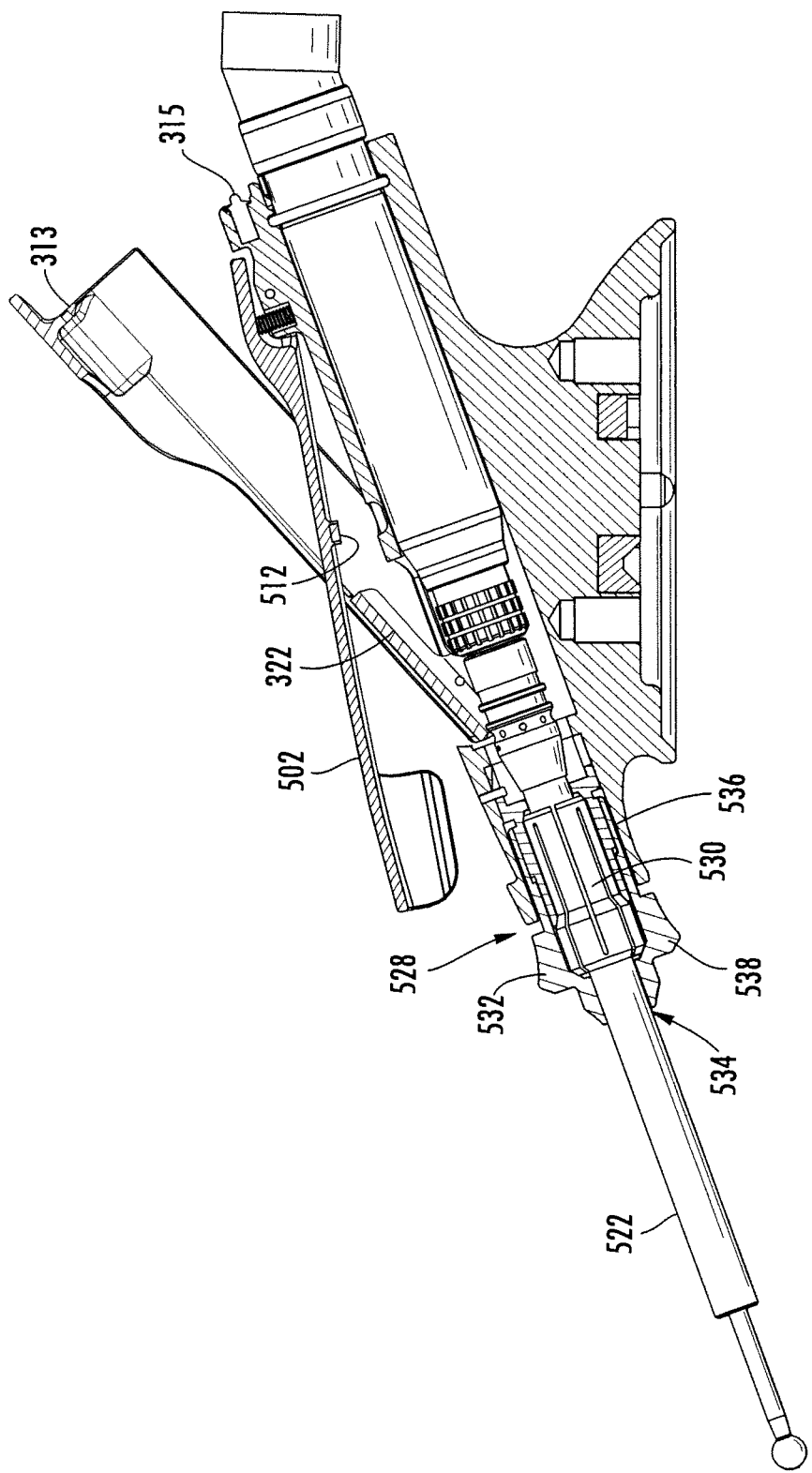
FIG. 14 is a cross sectional side view of the end effector assembly of FIG. 1 showing the interaction between the blocking feature and a hand switch when the release actuator is in the actuated position.

FIG. 14 shows a cross sectional view of the end effector 100 having the projection 322. As can be seen, with the release actuator 300 in the second position, the hand switch 502 would engage the projection 322 before being able to rotate downward about the pivot shaft 508 to a position where the magnet 512 would be close enough to the second sensor element for the second sensor element to detect the proximity of the magnet 512. As such, the release actuator 300 could be used to block the hand switch 502 from moving to a fully depressed position. In this manner, the projection 322 may function as a safety feature that reduces the likelihood that the motor 500 will be actuated when the release actuator 300 is in the second position.

According to an exemplary embodiment, the size of the collar 518 is relatively small and may be difficult for an operator to grasp, particularly if the operator is wearing gloves covered in bodily fluids from the surgical procedure. As such, the inclusion of the release actuator 300 enables an operator to actuate the collar 518 without having to physically grasp or directly engage the collar. Instead, the release actuator 300 enables the operator to actuate the collar 518 with a relatively upward, and short-range, lifting motion. Further, because the release actuator 300 is at least partially disposed outside of the housing 200, the operator is able to decouple the tool bit 400 from the motor 500 without having to remove the motor 500 from the housing 200 or otherwise disassemble the end effector 100. Such features may provide for a more efficient and precise process for decoupling an accessory from a device.

To position, support, and/or protect the tool bit 400, the end effector 100 may also include an attachment (e.g., sleeve, shield, etc.), shown as a support tube 522, that at least partially surrounds the tool bit 400. The support tube 522 may be particularly useful in applications where a considerable distance exists between the motor 500 and the operating head 406 of the tool bit 400. The support tube 522 shrouds or otherwise shields a central portion of the tool bit 400. In a surgical application, the support tube 522 advantageously prevents the rotating central portion of the tool bit 400 from contacting, and thereby potentially damaging, a patient's anatomy. The support tube 522 is coupled to the main body 202 of the housing 200 and extends between a first end 524 that is configured to be removably coupled to the motor 500 and a second end 526 that is configured to stop short of the operating head 406 of the tool bit 400. The support tube 522 is configured to be removably coupled to the end effector 100.

To secure the support tube 522 to the main body 202, the end effector 100 includes a second attachment mechanism 528. According to an exemplary embodiment, the second attachment mechanism 528 includes a collet 530 and a collet nut 532 for securing the support tube 522 to the main body 202. The collet nut 532 includes a first end 536 that is at least partially received within the front opening of the main body 202 at the neck 210 and a second end 538 provided forward of the neck 210. The first end 536 includes one or more external threads configured to engage one or more internal threads provided along an inner surface of the neck 210. The second end 538 defines a gripping surface configured to be engaged by an operator.

To secure the support tube 522 to the main body 202, the support tube 522 is inserted into a central aperture 534 defined by the collet 530 and the collet nut 352, after which the collet nut 532 is tightened down on the threaded end of the main body 202 by rotating the second end 538. As the collet nut 532 is tightened down on the threaded end of the main body 202, the collet 530 is compressed between the collet nut 532 and an outer surface of the support tube 522. The collet 530 is slotted and has a tapered end such that when the collet 530 is compressed between the collet nut 532 and the support tube 522, the collet 530 is compressed radially, causing the central aperture of the collet 530 to close tightly around the outer surface of the support tube 522. To remove the support tube 522 from the end effector 100, the collet nut 532 is loosened until the support tube 522 can be removed from the central aperture of the collet 530. According to the embodiment illustrated, the collet nut 532 is configured to be tightened and loosened by hand, without the aid of an additional tool. Further, the gripping surface of the collet nut 532 has a size and contour that make it relatively easy to be grasped by an operator.

Figure 15:
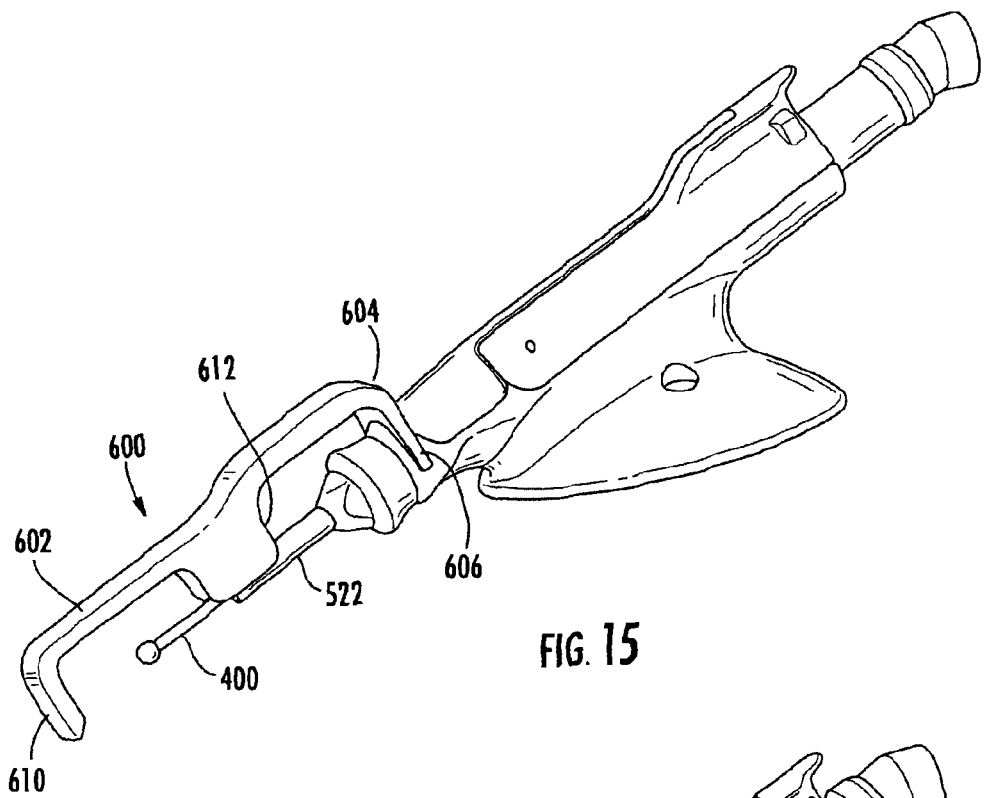
FIG. 15 is a perspective view of the end effector assembly of FIG. 1 shown with a removable length adjustment device according to an exemplary embodiment.
Figure 16:
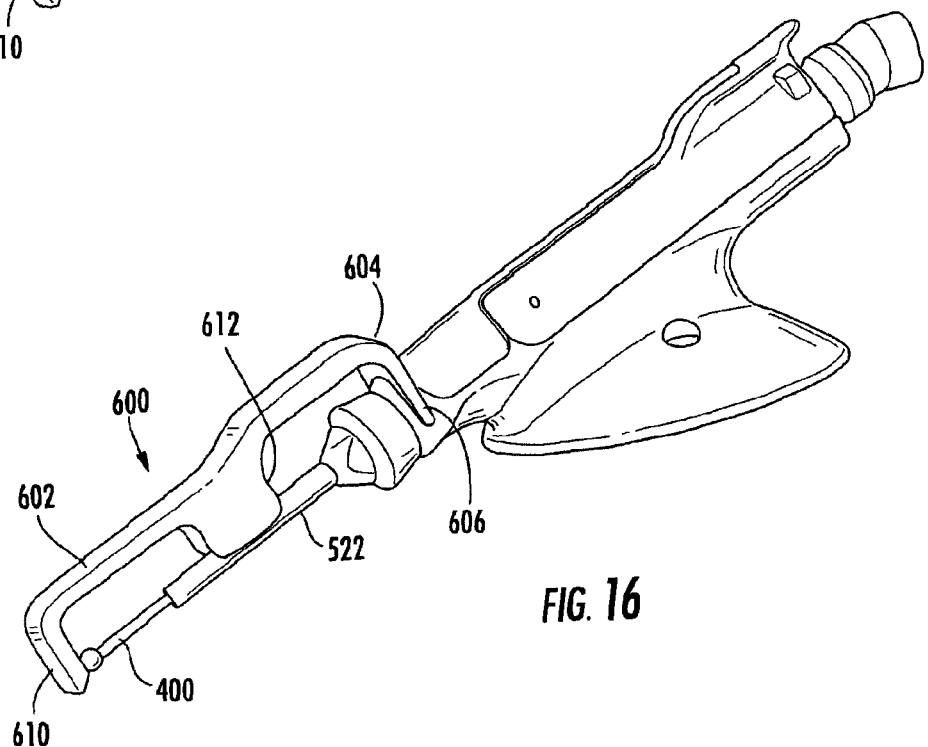
FIG. 16 is another perspective view of the end effector assembly of FIG. 1 shown with the removable adjustment device.

Referring to FIGS. 15 and 16, the end effector 100 may also include a guide mechanism (e.g., length adjustment tool, etc.) that can be used by an operator to set the tool bit 400 at a desired length relative to the housing 200. In certain applications the length of the tool bit 400 relative to the housing 200 needs to be controlled to ensure that the geometry to the operating head 406 is known. According to an exemplary embodiment, the guide mechanism is a bracket 600 that is configured to be selectively attachable to the housing 200.

The bracket 600 includes a first portion 602 that extends in a longitudinal direction of the tool bit 400 between a first end and a second end. Extending downward from the first end is a second portion 604 that is configured to be removably coupled to the housing 200. The second portion 604 includes a pair of engagement prongs 606 that are configured to be received within the recesses 234 (shown in FIG. 1) provided in the neck 210 of the main body 202. Extending downward from the second end of the first portion 602 is a third portion 610 that functions as a stop for the tool bit 400. The third portion 610 extends downward a distance sufficient for the tool bit 400 to contact the third portion 610 as the tool bit 400 is extended from the housing 200. The distance between the second portion 604 and the third portion 610 dictates the length that the tool bit 400 will extend from the housing 200. Such distance may vary depending on the application and/or the type of accessory being used. The bracket 600 is also shown as including a fourth portion 612 extending downward from the first portion 602 between the second portion 606 and the third portion 610. The fourth portion 612 is configured to rest on the support tube 522 to help the support bracket 600 when coupled to the end effector 100.

To set the length of the tool bit 400, the motor 500, the support tube 522, and the tool bit 400 are inserted into the end effector 100 with the collet nut 532 loose so that the support tube 522 and the tool bit 400 can slide relatively freely in an axial direction. With the motor 500, the support tube 522 and the tool bit 400 inserted, the bracket 600 is added to the end effector 100 by inserting the prongs 608 into the recesses 234. The motor 500, the support tube 522 and the tool bit 400 are then collectively moved such that the tool bit 400 extends an appropriate distance outward relative to the housing 200, i.e., until the operating head 406 contacts the third portion 610. At that point, the collet nut 532 is tightened and the bracket 600 can be removed from the end effector 100.

It is important to note that the terms used herein are intended to be broad terms and not terms of limitation. For purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may relate to a mechanical and/or electrical relationship between the two components.

It is also important to note that the construction and arrangement of the elements of the end effector as shown in the exemplary embodiments are illustrative only. Although only a few embodiments of the present invention have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the claims. Accordingly, all such modifications are intended to be included within the scope of the appended claims.

The order or sequence of any process or method steps may be varied or re-sequenced according to alternative embodiments. Other substitutions, modifications, changes and/or omissions may be made in the design, operating conditions and arrangement of the preferred and other exemplary embodiments without departing from the spirit of the present invention as expressed in the appended claims.

What is claimed is:

1. An end effector, comprising:
a tool including a drive configured to be coupled to and drive an engaging member for engaging a workpiece, and a release member configured to be displaced to permit decoupling of the engaging member from the drive;
a housing configured to receive at least a portion of the tool;
a release actuator disposed at least partially outside of the housing and coupled to the housing to permit movement between a first position and a second position to displace the release member to permit decoupling of the engaging member from the drive;
a drive actuator for actuating the drive, wherein the drive actuator is configured to be moveable relative to the housing between a non-actuated position and an actuated position;
wherein the release actuator includes an opening through which at least a portion of the drive actuator projects, and the release actuator is configured such that the drive actuator engages an end wall of the opening to prevent the drive actuator from moving to the actuated position when the release actuator is in the second position.

2. The end effector of claim 1, wherein the tool is a surgical tool.

3. The end effector of claim 1, wherein the release member is received within the housing.

4. The end effector of claim 1, wherein the release member is configured to be displaced by the release actuator axially along at least a portion of the tool to permit decoupling of the engaging member from the drive.

5. The end effector of claim 1, wherein the housing includes a fixing member configured to adjustably fix a position of the tool relative to the housing along an axial direction of the tool.

6. The end effector of claim 1, wherein the release actuator includes a moveable portion that extends at least partially outside the housing and that is configured to be moved relative to the housing.

7. The end effector of claim 6, wherein the moveable portion includes a lever configured to be rotated relative to the housing about a rotation axis and that is coupled to the housing at the rotation axis.

8. The end effector of claim 7, wherein rotation axis is substantially perpendicular to a central axis of the tool.

9. The end effector of claim 6, wherein the release actuator further includes a member configured to be moved in response to movement of the moveable portion relative to the housing.

10. The end effector of claim 9, wherein the member comprises a first cam that is configured to move through rotation in response to movement of the moveable portion relative to the housing.

11. The end effector of claim 10, wherein the member further comprises a second cam disposed on an opposite side of the tool from the first cam and that is configured to move through rotation in response to movement of the moveable portion relative to the housing.

12. The end effector of claim 1, wherein the release actuator is configured to prevent the drive actuator from moving to the actuated position when the release actuator is in the second position.

13. The end effector of claim 1, further comprising a base portion configured to attach to a joint.

14. The end effector of claim 13, wherein the end effector is configured to rotate at least partially about a first axis of rotation and at least partially about a second axis of rotation when the base portion is attached to the joint.

15. The end effector of claim 1, wherein the housing, release actuator, and drive actuator have a shape configured to be simultaneously grasped by a hand of a user.

16. A tool comprising:
a housing configured to at least partially receive a drive having a release member configured to be displaced axially along at least a portion of the tool to permit decoupling of an engaging member from the drive;
a first lever disposed at least partially outside of the housing and coupled to the housing about a first pivot shaft defining a first axis of rotation to permit movement between a first position and a second position to activate the drive; and
a second lever disposed at least partially outside of the housing and coupled to the housing about a second pivot shaft defining a second axis of rotation to permit movement between a third position and a fourth position to displace the release member to permit decoupling of the engaging member from the drive, the second axis of rotation being substantially parallel to the first axis of rotation
wherein the first lever rotates between the first position and the second position in a direction that is opposite a direction that the second lever rotates when moving between the third position and the fourth position; and
wherein the first lever is at least partially received within an aperture defined by the second lever.

17. The tool of claim 16, wherein the first pivot shaft is provided closer to a rear end of the housing and the second pivot shaft is provided closer to a front end of the housing.

18. The tool of claim 16, wherein the tool is an end effector.

19. The tool of claim 18, wherein the end effector is a surgical end effector.

20. The tool of claim 16, wherein the second lever includes a member that is received within the housing, and wherein the member comprises a first cam that is configured to move through rotation in response to movement of the second lever about the second pivot shaft.

21. The tool of claim 20, wherein the first cam is configured to engage the release member and displace the release member axially relative to the drive to permit decoupling of the engaging member from the drive.

22. The tool of claim 20, wherein the member further comprises a second cam disposed on an opposite side of the tool from the first cam and that is configured to move through rotation in response to movement of the second lever about the second pivot shaft.

23. A surgical tool comprising:
a housing;
a drive configured to be coupled to and drive an engaging member for engaging a workpiece;
a release member configured to be displaced to permit decoupling of the engaging member from the drive;
a release actuator disposed at least partially outside of the housing and coupled to the housing to permit movement between a first position and a second position to displace the release member to permit decoupling of the engaging member from the drive;
a drive actuator for actuating the drive;
wherein the drive actuator is configured to be moveable relative to the housing between a non-actuated position and an actuated position; and
wherein the release actuator includes an opening through which at least a portion of the drive actuator projects, and the release actuator is configured such that the drive actuator engages an end wall of the opening to prevent the drive actuator from moving to the actuated position when the release actuator is in the second position.

* * * * *